| United States Patent [19] | [11] | 4,233,228 |
|---|---|---|
| Mueller et al. | [45] | Nov. 11, 1980 |

[54] PURIFICATION OF TETRAHYDROFURAN

[75] Inventors: Herbert Mueller, Frankenthal; Otto H. Huchler, Limburgerhof, both of Fed. Rep. of Germany

[73] Assignee: BASF Aktiengesellschaft, Fed. Rep. of Germany

[21] Appl. No.: 952,805

[22] Filed: Oct. 19, 1978

[30] Foreign Application Priority Data

Oct. 31, 1977 [DE] Fed. Rep. of Germany ....... 2748788

[51] Int. Cl.³ .......................................... C07D 307/08
[52] U.S. Cl. .............................................. 260/346.11
[58] Field of Search ................................... 260/346.11

[56] References Cited

U.S. PATENT DOCUMENTS

| 2,790,813 | 4/1957 | Bente | 260/346.11 |
| 3,074,967 | 1/1963 | Brillhart | 260/346.11 |
| 3,221,030 | 11/1965 | Huffman | 260/346.11 |
| 3,980,672 | 9/1976 | Tomomatsu | 260/346.11 |

FOREIGN PATENT DOCUMENTS

| 700036 | 11/1940 | Fed. Rep. of Germany . |
| 2461922 | 7/1976 | Fed. Rep. of Germany . |
| 48-75563 | 10/1973 | Japan . |
| 49-5338 | 2/1974 | Japan . |
| 49-76861 | 7/1974 | Japan . |

OTHER PUBLICATIONS

Reppe et al., Annalender Chemie, 596 (1955) pp. 80-87.
Webster's Third New International Dictionary, G & C Merriam Co., Springfield, Mass. (1963) p. 232.

Primary Examiner—Richard Raymond
Attorney, Agent, or Firm—Keil & Witherspoon

[57] ABSTRACT

Tetrahydrofuran is purified by treatment with bleaching earth.

4 Claims, No Drawings

PURIFICATION OF TETRAHYDROFURAN

Tetrahydrofuran is an important solvent and intermediate for the chemical industry.

Depending on the intended use, tetrahydrofuran (THF) has to conform to varying standards of purity. Commercial technical-grade tetrahydrofuran is already very pure; normally, its purity is greater than 99.8%. However, for very demanding applications concentrations of impurities of as little as, for example, from 10 to 500 ppm may be detrimental.

Frequently, such contamination only arises subsequently, during storage and transportation of the solvent. For example, tetrahydrofuran very easily forms peroxides. If the product is handled without complete exclusion of air, peroxide formation is unavoidable. The decomposition of the peroxides subsequently leads to further contamination by carbonyl compounds.

The precise chemical structure of all by-products present in THF is not known and in general would not constitute worthwhile information. This is because in practice the method used to determine the degree of contamination is, in general, apart from gas-chromatographic analysis, the determination of characteristic data. This latter method is the more reliable for practical purposes. The most important characteristic data are obtained by determining the bromine number by the Kaufmann method, determining the carbonyl number by the hydroxylamine hydrochloride method and determining the peroxide content photometrically with titanyl sulfate.

It is an object of the present invention to provide a simple and cheap process for purifying technical-grade tetrahydrofuran. The process should be applicable regardless of whether the impurities have resulted from the synthesis or have arisen subsequently, for example through peroxide formation.

A plurality of processes for purifying tetrahydrofuran have already been proposed. For example, U.S. Pat. No. 3,980,672 proposes purifying tetrahydrofuran, contaminated specifically by n-butyraldehyde, by treatment with a molecular sieve having a pore size of from 0.4 to 0.5 nm and a heat of water adsorption of $1,800\pm100$ B.T.U./pound of $H_2O$. This method of purification, intended to deal with a specific impurity, is not a suitable method for simultaneously lowering the carbonyl number, the bromine number and the peroxide content. The same is true of Japanese Patent Application No. 74/005,338, which describes the removal of methanol from tetrahydrofuran by molecular sieves. According to Japanese Patent Application No. 74/076,861, acetaldehyde is removed from tetrahydrofuran by solid potassium hydroxide. Japanese Patent Application No. 73/075,563 describes the removal of aldehydes by treatment with ammonium sulfate. None of these disclosed methods achieves a simultaneous improvement in respect of the bromine number, carbonyl number and peroxide number. Furthermore, these methods have the disadvantage that the purifying agent employed is required in large amount and/or is more expensive.

We have found that the above object is achieved and that tetrahydrofuran can be purified to a point where the carbonyl number, the bromine number and the peroxide content approach 0, by simple treatment of tetrahydrofuran with bleaching earth. Crystallographically, bleaching earths and fuller's earths belong to the montmorillonites. They are colloidal, hydrated aluminum silicates in which the aluminum ions may be partially replaced by iron ions or magnesium ions. The ratio of silica to the oxides of divalent or trivalent metals in these minerals is about 4:1. The products are commercially available; they are in most cases activated by treatment with an acid, or are sold in the activated form, and are used widely for refining edible oils, fats and mineral oils.

Commercial bleaching earths normally contain from 4 to 8% of water. In this form, they are also used as catalysts or adsorbents. A further characteristic of the invention is that the most effective purification of tetrahydrofuran is achieved with bleaching earths which contain less than 3% of water, preferably 1% of water or less.

The production of dehydrated bleaching earths presents no difficulties. The water content of the earths can be reduced to less than 0.1% by heating at 110°–150° C. for from 1 to 8 hours.

The treatment according to the invention is simple and can be carried out inexpensively. Since the mechanism of the treatment, and the detailed nature of the trace impurities to be removed, is not known, it is frequently advisable generally to subject tetrahydrofuran to the treatment before it is used. Without the pre-treatment, adverse results may be achieved in applications which are sensitive to impurities.

Only small amounts of bleaching earth are required to treat tetrahydrofuran according to the invention. Advantageous results are achieved by using even as little as from 0.1 to 5% by weight, preferably from 0.5 to 3% by weight, based on THF, of the bleaching earth. Of course, THF can also be treated with larger amounts but this produces no further advantage. Frequently—as is also described in the Examples—the treatment can be repeated several times with the same bleaching earth, before the latter is spent.

To carry out the treatment, THF is intimately mixed with the bleaching earth. The duration of the treatment may be from 3 minutes to 12 hours, depending on the amount and the temperature. Preferably, treatment times of from 0.5 to 3 hours suffice; prolonged treatment has no adverse effect.

Since bleaching earths are normally in the form of fine powders or fine granules, they are mostly employed in the form of a suspension. In principle, it is also possible to employ the granules as a fixed bed, over which the tetrahydrofuran to be purified is passed.

The treatment may be carried out at room temperature, but preferably at an elevated temperature, for example at the boiling point of tetrahydrofuran. Temperatures of from 30° to 66° C. are preferred.

After the treatment with the bleaching earth, the latter is separated from the liquid in the conventional manner, using the conventional physical methods of separation. For example, it suffices to remove the solid by filtration or centrifuging. Another simple method of separation is to distil off the tetrahydrofuran. The treatment may be carried out continuously or batchwise. Continuous treatment is particularly advisable where a fixed bed is used for the purification treatment. If distillation is used to separate the liquid from the solid, the purifying agent left in the distillation residue can in general be re-used until its capacity is exhausted. Regeneration is in general not profitable; however, where desired, it can be carried out by heating at 150°–200° C. or by extraction with a suitable solvent.

EXAMPLE 1,000 parts by weight of technical-grade tetrahydrofuran are stirred for 2 hours at 64° C. with 20 parts of commercial bleaching earth sold under the name Tonsil Optimum FF ® (Süd-Chemie AG, Munich) which has been dehydrated to a water content of less than 0.1%. The liquid phase is then separated from the solid phase by distillation, without fractionation. The distillation residue, which is equal in weight to the Tonsil employed, is then used for 5 further purification treatments. As shown in the Table which follows, the purifying capacity of the bleaching earth is not exhausted even then.

Similar results were obtained if the solid was removed by filtration instead of effecting the separation by distillation, or if a different commercial product, for example "Katalysator KSF" (Süd-Chemie, Munich) was used, at the same concentration, as the bleaching earth.

| Purification treatment | Carbonyl number [mg of KOH/g] | Bromine number [g/100 g] | Peroxide content as $H_2O_2$ [ppm] |
|---|---|---|---|
| Untreated | 0.16 | 0.08 | 10 |
| 1 | <0.02 | <0.01 | 2 |
| 2 | <0.02 | 0.02 | 3 |
| 3 | 0.03 | 0.02 | 1 |
| 4 | <0.02 | 0.03 | 2 |
| 5 | 0.02 | 0.02 | <1 |
| 6 | 0.02 | 0.01 | 2 |

We claim:
1. A process for purifying tetrahydrofuran which comprises:
   intimately mixing the tetrahydrofuran to be treated at from room temperature to the boiling point of the tetrahydrofuran with a bleaching earth containing less than 3% by weight of water for from 3 minutes to 12 hours, and thereafter separating the bleaching earth from the tetrahydrofuran, whereby the carbonyl number, the bromine number and the peroxide content of the tetrahydrofuran are reduced.
2. The process of claim 1 wherein the bleaching earth contains less than one percent by weight of water.
3. The process of claim 1, wherein the amount of bleaching earth used is from 0.1 to 5% by weight, based on tetrahydrofuran.
4. The process of claim 1 wherein the treatment is carried out at a temperature of from 30° to 66° C.

* * * * *